United States Patent
Garnier et al.

(10) Patent No.: US 6,623,726 B2
(45) Date of Patent: Sep. 23, 2003

(54) PROCESS FOR PERMANENT RESHAPING OF HAIR

(75) Inventors: Nathalie Garnier, Scotch Plains, NJ (US); Dina Burakov, Springfield, NJ (US); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 65 days.

(21) Appl. No.: 09/725,519

(22) Filed: Nov. 30, 2000

(65) Prior Publication Data

US 2002/0094321 A1 Jul. 18, 2002

(51) Int. Cl.⁷ ................................................ A61K 7/09
(52) U.S. Cl. .................... 424/70.1; 424/70.4; 424/400; 424/401; 424/70.2
(58) Field of Search .................. 424/400, 401, 424/70.2, 70.4, 70.1

(56) References Cited

U.S. PATENT DOCUMENTS

| | | | |
|---|---|---|---|
| 1,572,027 A | | 2/1926 | Meyers |
| 1,701,459 A | * | 2/1929 | Cecelio ........................ 132/42 |
| 1,719,555 A | | 7/1929 | Lewis et al. |
| 1,746,018 A | | 2/1930 | Spaeth |
| 2,085,516 A | * | 6/1937 | Thomson .................... 132/36.2 |
| 2,140,243 A | * | 12/1938 | Moody et al. .............. 132/36.2 |
| 2,381,107 A | * | 8/1945 | Calabro ........................ 132/42 |
| 2,719,815 A | * | 8/1955 | Sanders ...................... 167/87.1 |
| 2,936,766 A | | 5/1960 | Beverly ........................ 132/39 |
| 3,465,759 A | * | 9/1969 | Haefele ......................... 132/7 |
| 3,871,388 A | | 3/1975 | Leoci ............................. 132/9 |
| 4,190,065 A | | 2/1980 | Kulpa |
| 4,353,380 A | | 10/1982 | Kolkmann .................... 132/40 |
| 4,942,892 A | | 7/1990 | Hill ............................... 132/247 |
| 5,813,419 A | | 9/1998 | Brams ........................ 132/222 |
| 5,824,384 A | | 10/1998 | Hickox |
| 5,932,201 A | | 8/1999 | de Labbey et al. ....... 424/70.17 |
| 6,116,250 A | * | 9/2000 | Buheitel ....................... 132/205 |

FOREIGN PATENT DOCUMENTS

| | | |
|---|---|---|
| EP | 039 072 | 4/1981 |
| EP | 787 444 | 8/1997 |
| FR | 649696 | 12/1928 |
| FR | 1153109 | 3/1958 |
| FR | 2416667 | 10/1979 |
| GB | 391 590 | 5/1933 |
| GB | 613 941 | 12/1948 |
| GB | 860 978 | 2/1961 |
| GB | 2194437 A * | 3/1988 |
| GB | 2194437 | 3/1988 |

OTHER PUBLICATIONS

Derwent Abstract, WPI Acc No. 1979–K8884B/197947 (1979).
International Search Report dated Sep. 17, 2002.

* cited by examiner

Primary Examiner—Thurman K. Page
Assistant Examiner—Rachel M. Bennett
(74) Attorney, Agent, or Firm—Finnegan, Henderson, Farabow, Garrett & Dunner, LLP

(57) ABSTRACT

A process for permanently modifying the shape of hair by wrapping hair in multilayered, deformable sheets of material comprising a first layer of a perforated, deformable, and semi-rigid material, and a second layer of material containing a thiol reducing composition in an amount effective for permanently modifying the shape of hair, wherein the first layer is placed on or attached to the second layer; providing a desired shape to the multilayered, deformable sheet of material which is wrapped around the hair; and applying an oxidizing composition comprising an oxidizing agent capable of reconstituting the disulfide bonds of the hair, wherein the oxidizing composition is applied either before or after liberating the hair from the multilayered, deformable sheet of material. In another variation, the hair is pre-treated with the reducing composition and then wrapped in a single deformable sheet for shaping. Multicomponent kits for use in the processes of the invention.

41 Claims, 1 Drawing Sheet

PROCESS FOR PERMANENT RESHAPING OF HAIR

The present invention relates to a process for treating keratinous material, for example the hair, for the purpose of obtaining a permanent reshaping of the hair. The process according to the invention is usable in professional hair salons, beauty salons, cosmetic salons and, significantly, by the consumer in his or her home without the assistance of a professional hair-stylist or cosmetologist.

Processes for providing durable modifications to the shape of the hair, such as permanent waving hair, are known in the art. The most common technique for obtaining a permanent reshaping of the hair consists, in a first stage, in opening the keratin —S—S—disulfide (cystine) bonds by applying a composition containing a reducing agent to the hair. Typically, the hair has been placed under tension beforehand with a device, usually a roller. This first stage is commonly referred to as the reduction step.

Following the reduction step, the hair is usually rinsed and, in a second stage, the disulfide bonds are reconstituted, giving the hair the desired shape, by applying to the hair an oxidizing composition. This second stage is typically known as the oxidation step, also known as the fixing step.

This process makes it equally possible either to make the hair wavy, to straighten it, or to remove its curliness. The new shape given to the hair by a chemical treatment such as described above is generally long-lasting and generally resists the action of washing with water or shampoos. This is in contrast to simple standard techniques for temporary reshaping, such as hairsetting.

The reducing compositions that have been used in order to carry out the first step of known permanent-waving processes generally contain, as reducing agents, sulphites, bisulphites or thiols. Typical thiols have included, for example, cysteine and the various derivatives thereof, cysteamine and the derivatives thereof, thiolactic acid, thioglycolic acid and the esters thereof, for example, glyceryl monothioglycolate, and thioglycerol.

A composition containing a reducing agent is intended to act chemically on the bonds that provide the cohesion of the protein structure of the hair: covalent disulfide cross-linkages, ionic bonds, or hydrogen bonds. The object of the reducing agent is to plasticize the hair fiber momentarily, rendering it deformable and without elasticity. In the case of a permanent-waving operation, the hair is rolled on curlers and then wetted with a reducing lotion, so that the imposed deformation is in the shape of curls.

After the hair has been reduced, a composition containing an oxidizing agent is applied and has the effect of restoring, or "fixing" the physicochemical structure to the hair fiber by forming new disulfide cross-links between keratin chains. The oxidizing composition is permitted to remain on the hair for a short period of time, usually about ten to fifteen minutes, after which the hair is unwound from the rollers and rinsed. The oxidizing composition is typically an acidic hydrogen peroxide solution. Other oxidizing agents used as fixatives include sodium perborate, potassium bromate, sodium chlorite, and sodium and potassium persulfates.

Variations of this process are also known. For example, the hair can be impregnated with a reducing composition before it is wound on rollers. Further, the reducing composition can contain additives such as disulfur or protecting agents, for example, cationic polymers, or other cosmetic agents, for example, silicones.

The processes of the prior art have a number of attendant disadvantages. For example, the user is required to wear gloves in order to avoid contact with the reducing lotion. Furthermore, the process requires a degree of expertise which may put off potential consumers, as the hair has to be wound on curlers. This process of winding the hair not only requires a certain degree of expertise, but it is also very time consuming. Accordingly, one aspect of the present invention is to provide for a faster, consumer-friendly, and durable modification of the shape of the hair. Another aspect of the invention is to provide a process for modifying the shape of the hair which can be performed by the consumer without the need for a professional hair stylist or cosmetologist. The process according to the invention can be at least one of practical, fast, and easy to use, so that no amount of expertise is required. Furthermore, the process according to the invention, can, in certain embodiments, allow one to avoid substantially all contact between the reducing composition and the skin.

The present invention, in one embodiment, relates to a process for permanently modifying the shape of hair, comprising providing a reducing composition comprising at least one thiol additionally comprising at least one function chosen from acid functions, amine functions, amide functions, and ester functions; providing a multilayered, deformable sheet of material comprising a first layer of a perforated, deformable, and semi-rigid material, and a second layer of material containing the reducing composition in an amount effective for permanently modifying the shape of hair, wherein the first layer is placed on or attached to the second layer to provide the multilayered, deformable sheet of material; wrapping at least one strand of hair with the multilayered, deformable sheet of material containing the reducing composition; providing a desired shape to the multilayered, deformable sheet of material which is wrapped around the at least one strand of hair; and applying to the at least one strand of hair, either before or after liberating the at least one strand of hair from the multilayered, deformable sheet of material, an oxidizing composition comprising an oxidizing agent capable of constituting new disulfide bonds on the hair; and rinsing the oxidizing composition from the hair.

A second embodiment of the invention relates to a process for permanently modifying the shape of the hair, comprising applying to at least one strand of hair a reducing composition comprising at least one thiol additionally comprising at least one function chosen from acid functions, amine functions, amide functions, and ester functions; shaping the at least one strand of hair by rolling, folding, or wrapping the at least one strand of hair with a deformable, semi-rigid sheet of material; and applying to the at least one strand, either before or after liberating the at least one strand of hair from the multilayered, deformable sheet of material, an oxidizing composition comprising an oxidizing agent capable of reconstituting new disulfide bonds on the hair; and rinsing the oxidizing composition from the hair.

A further embodiment of the invention relates to a multicomponent kit for permanently modifying the shape of the hair comprising at least three components which are separate from each other, a first component containing a reducing composition for reducing the disulfide bonds of a hair fiber, comprising at least one thiol additionally comprising at least one function chosen from acid functions, amine functions, amide functions, and ester functions; a second component containing a multilayered, deformable sheet of material comprising a first layer of a perforated, deformable, and semi-rigid material, and a second layer of material capable of containing the reducing composition, wherein the first layer is capable of being placed on or attached to the second layer; and a third component containing an oxidizing agent capable of forming new disulfide bonds on the hair fiber.

Yet another embodiment of the invention relates to a multicomponent kit for permanently modifying the shape of hair comprising at least three components which are separate from each other, a first component containing a reducing composition for reducing the disulfide bonds of a hair fiber, comprising at least one thiol additionally comprising at least one function chosen from acid functions, amine functions, amide functions, and ester functions; a second component containing a sheet of a deformable, semi-rigid material; and a third component containing an oxidizing agent capable of reforming the disulfide bonds of the hair fiber.

Another aspect of the invention relates to a multicomponent kit for permanently modifying the shape of hair comprising at least two components which are separate from each other, a first component containing a multilayered, deformable sheet of material comprising a first layer of a perforated, deformable, and semi-rigid material, and a second layer of material containing a reducing composition for reducing the disulfide bonds of a hair fiber, comprising at least one thiol additionally comprising at least one function chosen from acid functions, amine functions, amide functions, and ester functions, wherein the first layer is capable of being placed on or attached to the second layer; and a second component containing an oxidizing agent capable of forming new disulfide bonds on the hair fiber.

It is to be understood that both the foregoing general description and the following detailed description are exemplary and explanatory only and are not restrictive of the invention as claimed.

The accompanying drawings, which are incorporated in and constitute a part of this specification, illustrate one embodiment of the invention and, together with the description, serve to explain the principles of the invention.

Figure 1:
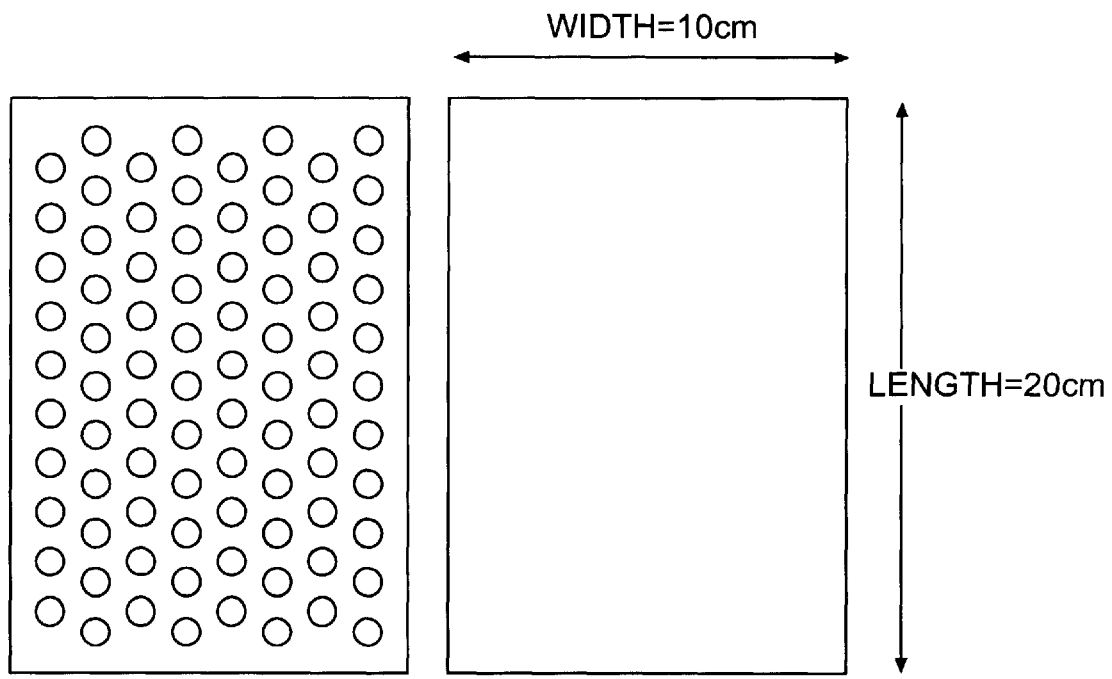
FIG. 1 shows a multilayered, deformable sheet comprising two layers of material, one of which is perforated, according to a first embodiment of the invention.

The processes of the present invention provide a reducing composition for use on the hair. The reducing compositions according to the process of the invention contain at least one thiol additionally comprising at least one function chosen from acid functions, amine functions, amide functions, and ester functions. Such thiols include, by way of non-limiting example, cysteine, dimercapto-adipic acid, thioglycolic acid, thiolactic acid, β-mercapto-propionic acid, monothioglycerol, thioglycolamide, glycol thioglycolate, glycerol thioglycolate, N-hydroxyethyl mercapto-acetamide, dimercapto-adipic acid, and cysteamine.

A first embodiment of the invention relates to a process for permanently modifying the shape of hair by providing a reducing composition as described above, and providing a multilayered, deformable sheet of material having a first layer of a perforated, deformable, and semi-rigid material and a second layer of material containing the reducing composition in an amount effective for permanently modifying the shape of the hair. The first layer is placed on or attached to the second layer. At least one strand of hair is wrapped in the multilayered, deformable sheet and the sheet (with the hair in it) is formed into a desired shape. Finally, an oxidizing composition comprising an oxidizing agent capable of constituting new disulfide bonds on the hair is applied, either before or after the hair is liberated from the multilayered, deformable sheet.

According to this first embodiment of the invention, the reducing composition may be in liquid or solid form. The solid reducing composition may contain the following ingredients:

5 to 100% by weight of at least one thiol additionally comprising at least one function chosen from acid functions, amine functions, amide functions, and ester functions;
  0 to 95% of pH regulating agents;
  0 to 95% of cationic polymers;
  0 to 95% of excipient (e.g., powder, soluble polymer);
  0 to 95% of a thickening agent (this allows the composition to have a gelled appearance when contacted with water);
  0 to 95% of a disulfur compound, such as dithiodiglycolic acid; and
  0 to 95% of a solvent According to one aspect of the invention, such a solid composition contains thioglycolic acid as the reducing agent and a nitrogen-containing alkali agent, such as ammonium hydroxide, as an additive. The solid composition may be mixed with water before use.

When the composition according to the first embodiment of the invention is in liquid form, the composition may contain from 0.2 to 80% by weight of a thiol additionally comprising at least one function chosen from acid functions, amine functions, amide functions, and ester functions. Such a composition may also, for example, contain the following additives in amounts by weight relative to the total weight of the composition:

0 to 80% of pH regulating agents;
  0 to 80% of cationic polymers;
  0 to 80% of excipient (e.g., powder soluble polymer);
  0 to 80% of a thickening agent
  0 to 80% of disulfur, such as dithiodiglycolic acid;
  20 to 99.8% of water;

According to one aspect of the invention, such a liquid reducing composition contains 1 to 16% thioglycolic acid, from 0 to 12% dithioglycolic diacid, from 0.1 to 3% of a thickening agent, and has a pH ranging from 6.2 to 10. According to another aspect of the invention, the composition is a gel The multilayered, deformable sheet used in the invention comprises two layers of material. The first layer is made of material that is synthetic or natural, such as cellulose, metal, or plastic. According to one aspect of the invention, the material of the first layer is aluminum, with or without surface treatment.

The second layer may be made of paper or other cellulosic material, treated or untreated. According to another aspect of the invention, the second layer is made of an absorbing material, natural or synthetic, for example cotton, sponge, or fiberglass. The second layer is typically the same or nearly the same length and width as the first layer. The second layer is designed to be capable of holding an amount of a thickened fluid, such as a reducing composition, e.g., in the form of a lotion, which is applied to the second layer by smearing or coating.

The layers can be any desired shape, such as rectangular or square. The dimensions of the layers, e.g., the length and width, can be adjusted according to, for example, the length and thickness of the strands of hair to be treated. According to one aspect of the invention, the layers are from 2 to 50 cm in length and 2 to 30 cm in width. The thickness of the layers may also vary. According an embodiment of the invention, whereby the shaping material comprises two layers, the thickness of a first layer is adjusted according to the type of material used, so that is it possible to deform it effortlessly in order to wind, wrap, roll, or fold the material around the strand(s) of hair. Once the new shape is set, the system does not spontaneously lose its shape, because the material stays in place.

As described above, the first layer is perforated. The number of perforations in a sheet can range from 5 to 200 perforations/dm$^2$. The perforations can range in diameter from 2 microns to 50 mm. According to one aspect of the invention, the perforations range in diameter from 0.5 mm to 5 mm.

The first layer may be attached to the second layer via at least one edge. It may also be simply maintained in place by contact with the reducing composition. Once the multilayered, deformable sheet is wrapped around at least one strand of hair, and as the desired shape is given to the deformable sheet which is wrapped around the at least one strand of hair, the perforations in the first layer allow the reducing agent in the second layer to contact the at least one strand of hair.

According to an embodiment of the invention, the reducing composition and multilayered, deformable sheet are used together in a process for providing a permanent modification to the shape of the hair. This process embodiment is performed by wrapping at least one strand of hair, optionally dry, with the multilayered, deformable sheet. A desired shape is then given to the whole set (the at least one strand of hair and the multilayered, deformable sheet) by wrapping, winding, and/or folding. The at least one strand of hair is permitted to remain in the desired shape for a period of time, for example 15 minutes, sufficient to permanently modify the shape of the hair. According to one aspect of this embodiment, the hair may be heated for a few minutes, if desired with, e.g., a hair dryer. Next, the strand of hair may be rinsed and then liberated from the multilayered, deformable sheet. Finally, an oxidizing composition comprising an oxidizing agent capable of constituting new disulfide bonds on the hair may be applied to the hair, and then rinsed from the hair. In one variation of this process, the hair is rinsed and the oxidizing composition applied prior to liberating the hair from the multilayered, deformable sheet. If this variation is employed, after application of the oxidizing agent, one waits wait for a period of time, often up to only a few minutes, before liberating the hair from the deformable sheet, to let the oxidizing agent have its effect. The step of subsequently rinsing the oxidizing agent from the hair is optional. Representative oxidizing agents useful according to the present invention include hydrogen peroxide, perborates, and persulfates, such as sodium perborate, potassium perborate, sodium persulfate, potassium persulfate, and sodium chlorite. In one embodiment the oxidizing agent is hydrogen peroxide.

According to one aspect of the invention, the hair is liberated from the multilayered, deformable sheet of material before the oxidizing composition is applied to the hair. According to another aspect of the invention, the hair is liberated from the multilayered, deformable sheet of material after the oxidizing composition is applied to the hair. According to yet another aspect of the invention, the hair is liberated from the multilayered, deformable sheet of material after rinsing the oxidizing composition from the hair.

Another embodiment of the invention relates to permanently modifying the shape of hair by applying to at least one strand of hair a reducing composition as described above, shaping the hair by rolling, folding, or wrapping the hair with a deformable, semi-rigid sheet of material, and then applying an oxidizing composition comprising an oxidizing agent capable of constituting new disulfide bonds on the hair, either before or after the hair is liberated from the deformable, semi-rigid sheet. According to this embodiment of the invention, the reducing composition may be the same as described earlier.

The deformable, semi-rigid sheet of this embodiment of the invention comprises a single sheet of material. The material can be synthetic or natural, such as metal or plastic. The material may be solid, perforated, or woven. According to one aspect of the invention, the material is aluminum, with or without surface treatment. The sheet can be any desired shape, such as rectangular or square. The dimensions of the sheet, e.g., the length and width, can be adjusted according to, for example, the length and thickness of the strands of hair to be treated. According to one aspect of the invention, the sheets are from 2 to 50 cm in length and 2 to 30 cm in width.

The thickness of the sheet may vary according to the type of material used, so that it is possible to deform the sheet effortlessly in order to wrap, wind, roll, and/or fold the sheet around the strand(s) of hair. Thus, once the new shape is set, the sheet does not spontaneously lose its shape.

According to one aspect of this embodiment, the sheet is perforated. The number of perforations in a sheet can range from 5 to 200 perforations/dm$^2$. The perforations can range in diameter from 2 microns to 50 mm.

The particular process for permanently modifying the shape of the hair, according to this embodiment of the invention, includes pretreating the hair (either part of the hair or the whole head of hair) with a reducing composition, as described herein. The pretreated hair is then wrapped with the deformable, semi-rigid sheet of the second embodiment of the invention. The desired shape is given to the entire hair (the pretreated hair strand and the deformable, semi-rigid sheet) by rolling, winding, and/or folding. The hair is permitted to remain in the desired shape for a period of time, for example 15 minutes, sufficient to permanently modify the shape of the hair. During this period of time the hair may be heated, if desired. The heating may be performed with a hair dryer. Finally, an oxidizing composition as described above is applied to the hair, and then rinsed.

According to one aspect of this embodiment of the invention, the hair is liberated from the multilayered, deformable sheet of material before the oxidizing composition is applied to the hair. According to another aspect of this embodiment of the invention, the hair is liberated from the multilayered, deformable sheet of material after the oxidizing composition is applied to the hair. According to a third aspect of this embodiment of the invention, the hair is liberated from the multilayered, deformable sheet of material after rinsing the oxidizing composition from the hair.

Suitable pH regulating agents may be chosen, for example, from ornithine, lysine, arginine, and salts thereof. The pH regulating agents may be used alone or as a mixture. They may also be present with other pH regulating agents such as, for example, aqueous ammonia, monoethanolamine, and carbonate-based products.

The cationic polymers used in the present invention contain primary, secondary, tertiary, or quaternary amine groups in the main chain. They generally have a molecular weight of greater than 500. According to one aspect of the invention, the cationic polymers have a molecular weight greater than 500, such as 1000.

The cationic polymers for use according to the present invention may be chosen from, for example:

(1) polymers comprising piperazinyl units and divalent alkylene or hydroxyalkylene radicals containing straight or branched chains, which are optionally interrupted by oxygen, sulphur or nitrogen atoms, or by aromatic or heterocyclic rings, as well as the oxidation and/or quaternization products of these polymers. Such polymers are described in particular in French Patent Nos. 2,162,025 and 2,280,361, which are specifically incorporated by reference herein;

(2) water-soluble polyamino amides which may be prepared by polycondensation of an acidic compound with a polyamine; these polyamino amides may be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or, alternatively, with an oligomer resulting from the reaction of a difunctional compound which is reactive towards a bis-halohydrin, a bis-azetidinium, a bis-haloacyidiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides may be alkylated or, if they contain one or more tertiary amine functions, they may be quaternized. Such polymers are described in particular in French Patent Nos. 2,252,840 and 2,368,508, which are specifically incorporated herein by reference.

(3) polyamino amide derivatives resulting from the condensation of at least one polyalkylene polyamine with at least one polycarboxylic acid followed by alkylation with at least one difunctional agent. Polyaminoamide derivatives, for example, may be chosen from adipic acid-dialkylaminohydroxyalkyl-dialkylenetriamine polymers in which the alkyl radical contains from 1 to 4 carbon atoms and may denote methyl, ethyl or propyl. Such polymers are described in particular in French Patent No. 1,583,363, which is specifically incorporated herein by reference. In one embodiment, the polyamino derivatives may be chosen from adipic acid/dimethylaminohydroxypropyl/diethylenetriamine polymers sold under the name CARTARETINE F, F4 or F8 by Sandoz.

(4) polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranges from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1. Such polymers are described in particular in U.S. Pat. Nos. 3,227,615 and 2,961,347, which are specifically incorporated herein by reference. Polymers of this type are marketed in particular under the name HERCOSETT 57 by Hercules Inc., or alternatively under the name PD 1/0 or DELSEFTE 101 by Hercules in the case of the adipic acid/epoxypropyl/diethylenetriamine copolymer.

(5) cyclohomopolymers of methyldiallylamine or of dimethyldiallylammonium, including for example homopolymers containing, as main chain constituents, units corresponding to the formulae (I) or (II):

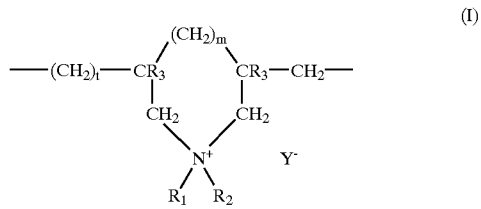

(I)

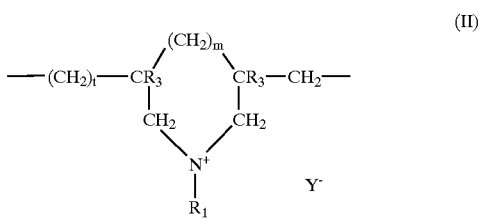

(II)

in which formulae:

m and t are equal to 0 or 1, the sum m+t being equal to 1; $R_3$ are identical or different and each is chosen from a hydrogen atom and a methyl radical; $R_1$ and $R_2$ are identical or different and each is chosen from alkyl groups having from 1 to 22 carbon atoms, hydroxyalkyl groups in which the alkyl group has 1 to 5 carbon atoms, and lower amidoalkyl groups, or $R_1$ and $R_2$ may be chosen from, together with the nitrogen atom to which they are attached, heterocyclic groups, such as piperidyl or morpholinyl; and $Y^-$ is an anion chosen from bromide, chloride, acetate, borate, citrate, tartrate, bisulphate, bisulphite, sulphate, and phosphate.

In one embodiment, cyclohomopolymers of dimethyldiallylammonium may be chosen from dimethyldiallylammonium chloride sold under the name MERQUAT 100 by Merck. These polymers are described in particular in French Patent No. 2,080,759 and in its Certificate of Addition 2,190,406, both of which are specifically incorporated by reference herein.

(6) quaternary diammonium polymers containing repeating units corresponding to the formula:

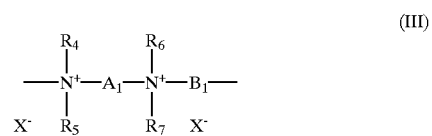

(III)

in which: $R_4$, $R_5$, $R_6$ and $R_7$ are identical or different and each is chosen from aliphatic radicals comprising from 1 to 20 carbon atoms, alicyclic radicals comprising up to 20 carbon atoms, arylaliphatic radicals comprising up to 20 carbon atoms and lower hydroxyalkylaliphatic radicals, or alternatively $R_4$, $R_5$, $R_6$ and $R_7$, together or separately, constitute, with the nitrogen atoms to which they are attached, heterocycles optionally containing a second hetero atom other than nitrogen or, alternatively, $R_4$, $R_5$, $R_6$ and $R_7$ are identical or different and each is chosen from linear and branched C1–C6 alkyl radicals substituted with at least one substituent chosen from nitrile, esters, acyls, amides, —CO—O—$R_8$—D, and —CO—NH—$R_8$—D radicals, where $R_8$ is chosen from alkylenes and D is chosen from quaternary ammonium groups; $A_1$ and $B_1$ are identical or different and each is chosen from linear and branched, saturated and unsaturated, polymethylene groups containing from 2 to 20 carbon atoms and which may contain, bonded to or intercalating in the main chain, at least one entity chosen from aromatic rings, oxygen atoms, sulphur atoms and groups chosen from sulphoxide, sulphone, disulphide, amino, alkylamino, hydroxyl, quaternary ammonium, ureido, amide and ester groups; $X^-$ denotes an anion derived from an acid chosen from inorganic and organic acids; $A_1$, $R_4$, and $R_6$ may form, together with the two nitrogen atoms to which they are attached, a piperazinyl ring; in addition, if $A_1$ is chosen from linear and branched, saturated and unsaturated alkylene and hydroxyalkylene radicals, $B_1$ may also be chosen from $—(CH_2)_n—CO—D—OC—(CH_2)_n—$ groups in which D is chosen from: a) glycol residues of formula: $O—Z—O—$, where Z is chosen from linear and branched hydrocarbon radicals and groups corresponding to one of the following formulae: number ranging from 1 to 4 representing an average degree of polymerization; b) bis-secondary diamine residues such as a piperazine derivative; c) bis-primary diamine residues of formula: $—NH—Y—NH—$, where Y is chosen from linear and branched hydrocarbon radicals, or alternatively the divalent radical

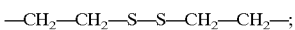

and d) a ureylene group of formula: $—NH—CO—NH—$. $X^-$ is an anion such as chloride or bromide. These polymers generally have a molecular mass ranging from 1000 to 100,000. Polymers of this type are described in particular in French Patent Nos. 2,320,330, 2,270,846, 2,316,271, 2,336,434 and 2,413,907, and U.S. Pat. Nos. 2,273,780, 2,375,853, 2,388,614, 2,454,547, 3,206,462, 2,261,002, 2,271,378, 3,874,870, 1,001,432, 3,929,990, 3,966,904, 4,005,193, 4,025,617, 4,025,627, 4,025,653, 1,026,945 and 4,027,020, all of which are specifically incorporated by reference herein.

(7) quaternary polyammonium polymers comprising units of formula (IV):

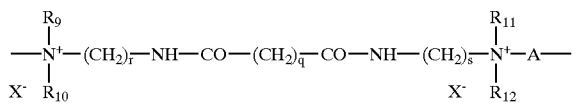

in which: $R_9$, $R_{10}$, $R_{11}$ and $R_{12}$ are be identical or different and each is chosen from a hydrogen atom and radicals chosen from methyl, ethyl, propyl, β-hydroxyethyl, β-hydroxypropyl and $—CH_2CH_2(OCH_2CH_2)_pOH$ radicals; where p is equal to an integer ranging from 0 to 6, with the proviso that $R_9$, $R_{10}$, $R_{11}$ and $R_{12}$ do not simultaneously represent a hydrogen atom; r and s, which may be identical or different, are integers from 1 to 6; q is equal to an integer ranging from 0 to 34; $X^-$ is chosen from halogen atoms; and A is chosen from dihalide radicals and $—CH_2—CH_2—O—CH_2—CH_2—$. Such compounds are described in particular in European Patent Application No. EP-A-122,324, which is incorporated by reference herein. In one embodiment, quaternary polyammonium polymers may be chosen from, for example, the products MIRAPOL A 15, MIRAPOL AD1, MIRAPOL AZ1 and MIRAPOL 175 sold by Miranol. In a further embodiment, quaternary polyammonium polymers may be chosen from MERQUAT 100 and the compound of formula (III) in which $R_4$, $R_5$, $R_6$ and $R_7$ represent a methyl radical, $A_1$ represents a radical of formula $—(CH_2)_3—$, $B_1$ represents a radical of formula $—(CH_2)_6—$ and $X^-$ represents a chloride anion (referred to hereinafter as MEXOMER PO).

The reducing composition may also contain at least one treating ingredient chosen from waxes, swelling agents, penetration agents, and agents which allow the effectiveness of the reducing agent to be reinforced, for example dimethylisosorbitol, urea and derivatives thereof, pyrrolidone, N-alkylpyrrolidones, thiamorpholinone, alkyl ethers of alkylene glycol or of dialkylene glycol such as, for example, propylene glycol monomethyl ether, dipropylene glycol monomethyl ether, ethylene glycol monoethyl ether and diethylene glycol monoethyl ether, C3–C6 alkanediols such as, for example, 1,2-propanediol and 1,2-butanediol, 2-imidazolidinone and other compounds such as fatty alcohols, lanolin derivatives, active ingredients such as pantothenic acid, agents for preventing hair loss, antidandruff agents, thickeners, suspension agents, sequestering agents, opacifiers, dyes and sunscreens, as well as fragrances and preserving agents.

The compositions may also be in so-called "self-neutralizing" or alternatively "self-regulating" form and, in this case, the reducing agents are combined with at least one disulphide (also referred to as one "disulphur") for its use in a self-neutralizing permanent-waving reducing composition. The at least one disulphide may be chosen from, for example, dithiodiglycolic acid, dithioglycerol, cystamine, N,N'-diacetylcystamine, cystine, pantethine and the disulphides of the N-(mercaptoalkyl)-ω-hydroxyalkylamides described in European Patent Application No. EP-A-354,835, which is specifically incorporated herein by reference, the disulphides of the 4-N-mono or 4-N,N-dialkylmercaptobutyramides described in European Patent Application No. EP-A-368,763, which is specifically incorporated herein by reference, the disulphides of the amino-mercaptoalkylamides described in European Patent Application No. EP-A-432,000, which is specifically incorporated herein by reference, the disulphides of the derivatives of the N-(mercaptoalkyl)succinamic acids or of the N-(mercaptoalkyl) succinimides described in European Patent Application No. EP-A-465,342, which is specifically incorporated herein by reference, and the disulphides of the alkylaminomercaptoalkylamides described in European Patent Application No. EP-A-514,282, which is specifically incorporated herein by reference. These disulphides are generally present in a molar ratio ranging from 0.5 to 2.5 and, according to one aspect of the invention, are present in a molar ratio ranging from 1 to 2 relative to the reducing agent (see U.S. Pat. No. 3,768,490, which is specifically incorporated herein by reference).

The invention also provides for a multicomponent kit for permanently modifying the shape of the hair, wherein the kit comprises at least three separate components. One component of the kit contains a composition comprising the reducing composition. A second component of the kit contains the single or multilayered, deformable sheet of material. The third component of the kit contains an oxidizing agent capable of forming new disulfide bonds on the hair. The skilled artisan, based on the stability of the composition and the application envisaged, will be able to determine how the composition and/or multicomponent compositions should be stored and mixed.

Another kit comprises two separate components. One component of the kit contains the single or multilayered deformable sheet of material with the reducing composition. The second component of the kit contains an oxidizing agent capable of forming new disulfide bonds on the hair.

The examples which follow are given by way of non-limiting illustration of the present invention.

EXAMPLES

Example 1
Composition C1—Gelled Reducing Lotion

| | |
|---|---|
| Thiolglycolic acid (TGA) | 9% |
| Disulfur of TGA | 6% |
| Sequestering agent | q.s. |
| Thickening agent (guar gum) | q.s. |
| Base (ammonium hydroxide) | q.s. to pH 9 |
| Water | q.s. to 100% |

The reducing lotion C1 was applied as part of a process for permanently modifying the hair, as set forth below:

A deformable, multilayered sheet was made of the association of two layers glued to each other. Each of the two layers was 10×15 cm. The first layer was made of a deformable, semi-rigid material (aluminum foil), and was perforated at 100 holes/dm$^2$ (see FIG. 1). The second layer was made of a permeable material (paper) holding the reducing lotion C1. The second layer was coated with 3 g of the gelled reducing lotion C1 per dm$^2$.

Figure 2:
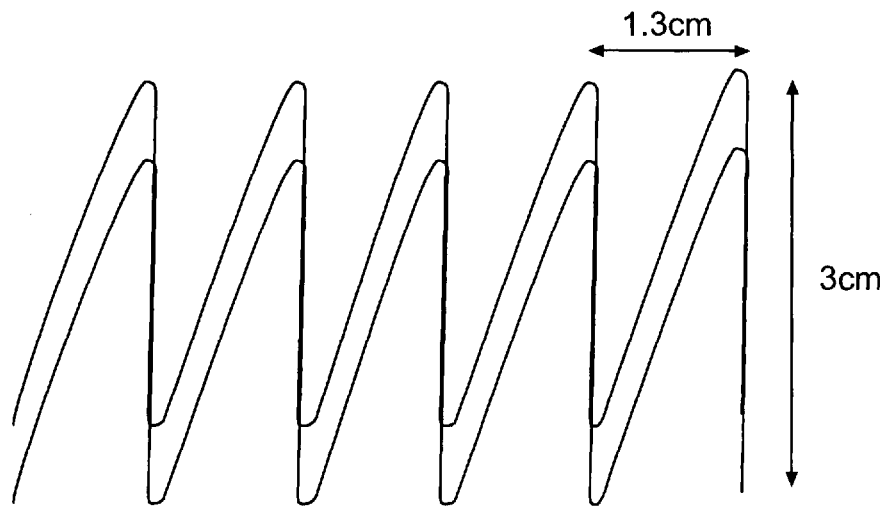
FIG. 2 shows the folded shape provided to the hair according to Example 2 of the invention, set forth in detail below.

The multilayered, deformable sheet was then applied to dry hair by wrapping it around strands of hair. Each unit comprising the strand(s) of dried hair enclosed within the multilayered sheet was then shaped by hand by folding the unit in an accordion fashion (see FIG. 2). The shaped units were then permitted to stand for 15 minutes, and were heated with a hair dryer for four minutes. The strands of hair were then rinsed and liberated from the units. At this point a hydrogen peroxide lotion was applied to the entire head of hair for five minutes, and the hair was then rinsed.

Results

The hair was shaped in a durable fashion according to the desired shape. The whole hair showed folds at regular 2 cm intervals. The resulting shape resisted shampooing.

Example 2
Composition C2—Gelled reducing lotion

| | |
|---|---|
| Thiolglycolic acid | 9% |
| Disulfur of TGA | 6% |
| Sequestering agent | q.s. |
| Thickening agent (guar gum) | q.s. |
| Base (ammonium hydroxide) | q.s. to pH 9 |
| Water | q.s. to 100% |

A deformable, semi-rigid sheet of aluminum foil allowing for an easy deformation of the shape of the hair was used. The sheet had dimensions of 10×15 cm, and was perforated (100 perforations/dm$^2$) in order to allow for rinsing of the hair.

60 ml of composition C2 was applied to dry hair. The strands of hair were then wrapped with the aluminum sheets. The hair was then shaped by hand folding, and was permitted to stand for 15 minutes. The hair was then rinsed and liberated from the sheets. Lastly, a hydrogen peroxide lotion was applied to the hair for five minutes in order to constitute new disulfide bonds, and the hair was then rinsed.

Results

The hair was durably deformed into the desired shape, showing regular folds every 2 cm. The hair had a soft and silky feel.

The described embodiments are to be considered in all respects as illustrative only and not restrictive. The scope of the invention is, therefore, indicated by the appended claims, rather than by the foregoing description. All changes which come within the meaning and range of equivalency of the claims are to be embraced within their scope.

What is claimed is:

1. A process for permanently modifying the shape of hair, comprising:
   (i) providing a reducing composition comprising at least one thiol additionally comprising at least one function chosen from acid functions, amine functions, amide functions, and ester functions;
   (ii) providing a multilayered, deformable sheet of material comprising a first layer of a perforated, deformable, and semi-rigid material, and a second layer of material containing said reducing composition in an amount effective for permanently modifying the shape of hair, wherein said first layer is placed on or attached to said second layer to provide said multilayered, deformable sheet of material;
   (iii) wrapping at least one strand of hair with the multilayered, deformable sheet of material containing said reducing composition;
   (iv) providing a desired shape to the multilayered, deformable sheet of material which is wrapped around said at least one strand of hair;
   (v) applying an oxidizing composition comprising an oxidizing agent capable of constituting new disulfide bonds on the hair, wherein said oxidizing composition is applied either before or after liberating the at least one strand of hair from the multilayered, deformable sheet of material; and
   (vi) rinsing the oxidizing composition from the hair.

2. The process according to claim 1, wherein said at least one thiol is chosen from cysteine, dimercapto-adipic acid, thioglycolic acid, thiolactic acid, β-mercapto-propionic acid, monothioglycerol, thioglycolamide, glycol thioglycolate, glycerol thioglycolate, N-hydroxyethyl mercapto-acetamide, dimercapto-adipic acid, and cysteamine.

3. The process according to claim 1, wherein said reducing composition further comprises at least one additive chosen from pH regulating agents, cationic polymers, excipients, thickening agents, disulfur, and solvents.

4. The process according to claim 1, wherein the reducing composition is in the form of a liquid.

5. The process according to claim 4, wherein the reducing composition comprises said at least one thiol in an amount ranging from 0.2 to 40% by weight relative to the total weight of the composition.

6. The process according to claim 5, wherein the reducing composition comprises thioglycolic acid, dithiodiglycolic diacid, and a thickening agent, and has a pH ranging from 6.2 to 10.

7. The process according to claim 1, wherein the reducing composition is in the form of a solid.

8. The process according to claim 7, wherein said reducing composition comprises said at least one thiol in an amount ranging from 5 to 100% by weight relative to the total weight of the composition.

9. The process according to claim 1, wherein said oxidizing agent is chosen from hydrogen peroxide, sodium perborate, potassium bromate, sodium chlorite, and sodium persulfate and potassium persulfate.

10. The process according to claim 9, wherein said oxidizing agent is hydrogen peroxide.

11. The process according to claim 1, further comprising applying heat to the at least one strand of hair while it is wrapped in the multilayered, deformable sheet of material.

12. The process according to claim 1, further comprising rinsing said at least one strand of hair prior to applying said oxidizing composition.

13. The process according to claim 1, wherein said perforated, deformable and semi-rigid material of said first layer is chosen from cellulose, metals, plastics and natural materials.

14. The process according to claim 1, wherein said perforated, deformable and semi-rigid material is aluminum, which may or may not be surface-treated.

15. The process according to claim 1, wherein said material comprising said second layer is chosen from cellulose derivatives and synthetic and natural absorbent materials.

16. The process according to claim 15, wherein said cellulose derivatives and absorbent materials are chosen from paper, cotton, sponge, and fiberglass.

17. The process according to claim 1, wherein said perforated, deformable and semi-rigid material of said first layer has at least 5 perforations per $dm^2$.

18. The process according to claim 1, wherein said at least one strand of hair is left to stand wrapped in said shaped, multilayered deformable sheet for a time sufficient to permanently modify the shape of said hair.

19. The process according to claim 18, wherein said at least one strand of hair is left to stand wrapped in said shaped, multilayered deformable sheet for a period of time ranging from 10 to 20 minutes.

20. The process according to claim 1, wherein the at least one strand of hair is liberated from the multilayered, deformable sheet of material before said oxidizing composition is applied to said at least one strand of hair.

21. The process according to claim 1, wherein the at least one strand of hair is liberated from the multilayered, deformable sheet of material after said oxidizing composition is applied to said at least one strand of hair.

22. The process according to claim 1, wherein the at least one strand of hair is liberated from the multilayered, deformable sheet of material after rinsing said oxidizing composition from said at least one strand of hair.

23. A process for permanently modifying the shape of hair, comprising:
  (i) applying to at least one strand of hair a reducing composition comprising at least one thiol additionally comprising at least one function chosen from acid functions, amine functions, amide functions, and ester functions;
  (ii) shaping said at least one strand of hair by winding, rolling, folding, or wrapping the at least one strand of hair with a deformable, semi-rigid sheet of material;
  (iii) applying an oxidizing composition comprising an oxidizing agent capable of constituting new disulfide bonds on the hair, wherein said oxidizing composition is applied either before or after liberating said at least one strand of hair from the deformable semi-rigid sheet of material; and
  (vi) rinsing the oxidizing composition from the hair.

24. The process according to claim 23, wherein said reducing composition comprises said at least one thiol in an amount ranging from 0.2 to 40% by weight relative to the total weight of the composition.

25. The process according to claim 23, wherein said reducing composition further comprises at least one additive chosen from pH regulating agents, cationic polymers, excipients, thickening agents, disulfur, and solvents.

26. The process according to claim 24, wherein the reducing composition comprises thioglycolic acid and dithiodiglycolic diacid, and has a pH ranging from 6.2 to 10.

27. The process according to claim 23, wherein said oxidizing agent is chosen from hydrogen peroxide, sodium perborate, potassium bromate, sodium chlorite, and sodium persulfate and potassium persulfate.

28. The process according to claim 24, wherein the oxidizing agent is hydrogen peroxide.

29. The process according to claim 23, further comprising applying heat to the at least one strand of hair while it is wrapped in the deformable sheet of material.

30. The process according to claim 23, further comprising rinsing said at least one strand of hair prior to applying said oxidizing composition.

31. The process according to claim 23, wherein said deformable, semi-rigid sheet of material is chosen from cellulose, metals, plastics and natural materials.

32. The process according to claim 23, wherein said deformable, semi-rigid sheet of material is aluminum, which may or may not be surface-treated.

33. The process according to claim 23, wherein said deformable, semi-rigid material is perforated with at least 5 perforations per $dm^2$.

34. The process according to claim 23, wherein said at least one strand of hair is left to stand wrapped in said shaped, deformable sheet for a time sufficient to permanently modify the shape of said hair.

35. The process according to claim 34, wherein said at least one strand of hair is left to stand wrapped in said shaped, deformable sheet for a period of time ranging from 10 to 20 minutes.

36. The process according to claim 23, wherein the at least one strand of hair is liberated from the multilayered, deformable sheet of material before said oxidizing composition is applied to said at least one strand of hair.

37. The process according to claim 23, wherein the at least one strand of hair is liberated from the multilayered, deformable sheet of material after said oxidizing composition is applied to said at least one strand of hair.

38. The process according to claim 23, wherein the at least one strand of hair is liberated from the multilayered, deformable sheet of material after rinsing said oxidizing composition from said at least one strand of hair.

39. A multicomponent kit for permanently modifying the shape of hair comprising at least three components which are separate from each other,
  a first component containing a reducing composition for reducing the disulfide bonds of a hair fiber, comprising at least one thiol additionally comprising at least one function chosen from acid functions, amine functions, amide functions, and ester functions;
  a second component containing a multilayered, deformable sheet of material comprising a first layer of a perforated, deformable, and semi-rigid material, and a second layer of material capable of containing the reducing composition, wherein said first layer is capable of being placed on or attached to said second layer;
  a third component containing an oxidizing agent capable of forming new disulfide bonds on the hair fiber.

40. A multicomponent kit for permanently modifying the shape of hair comprising at least three components which are separate from each other,
  a first component containing a reducing composition for reducing the disulfide bonds of a hair fiber, comprising at least one thiol additionally comprising at least one function chosen from acid functions, amine functions, amide functions, and ester functions;

a second component containing a sheet of a deformable, semi-rigid material;

a third component containing an oxidizing agent capable of reforming the disulfide bonds of the hair fiber.

41. A multicomponent kit for permanently modifying the shape of hair comprising at least two components which are separate from each other, a first component containing a multilayered, deformable sheet of material comprising a first layer of a perforated, deformable, and semi-rigid material, and a second layer of material containing the reducing composition for reducing the disulfide bonds of a hair fiber, comprising at least one thiol additionally comprising at least one function chosen from acid functions, amine functions, amide functions, and ester functions, wherein said first layer is capable of being placed on or attached to said second layer;

a second component containing an oxidizing agent capable of forming new disulfide bonds on the hair fiber.

* * * * *

UNITED STATES PATENT AND TRADEMARK OFFICE
CERTIFICATE OF CORRECTION

PATENT NO.    : 6,623,726 B2
DATED         : September 23, 2003
INVENTOR(S)   : Garnier et al.

It is certified that error appears in the above-identified patent and that said Letters Patent is hereby corrected as shown below:

Title page,
Item [*] Notice, should read, -- ... the term of this patent is extended or adjusted under 35 U.S.C. 154(b) by 80 days. --

Signed and Sealed this

Fifth Day of October, 2004

JON W. DUDAS
*Director of the United States Patent and Trademark Office*